(12) United States Patent
Wang et al.

(10) Patent No.: US 10,265,280 B2
(45) Date of Patent: Apr. 23, 2019

(54) FORMULATIONS FOR THE TREATMENT OF OCULAR SURFACE DISEASES AND RELATED METHODS

(71) Applicants: Mingwu Wang, Tucson, AZ (US); Cindy A Wang, Tucson, AZ (US)

(72) Inventors: Mingwu Wang, Tucson, AZ (US); Cindy A Wang, Tucson, AZ (US)

(*) Notice: Subject to any disclaimer, the term of this patent is extended or adjusted under 35 U.S.C. 154(b) by 0 days.

(21) Appl. No.: 15/809,659

(22) Filed: Nov. 10, 2017

(65) Prior Publication Data

US 2018/0133173 A1 May 17, 2018

Related U.S. Application Data

(60) Provisional application No. 62/463,717, filed on Feb. 26, 2017, provisional application No. 62/421,822, filed on Nov. 14, 2016.

(51) Int. Cl.
*A61K 31/137* (2006.01)
*A61K 9/08* (2006.01)
*A61K 47/02* (2006.01)

(52) U.S. Cl.
CPC .............. *A61K 31/137* (2013.01); *A61K 9/08* (2013.01); *A61K 47/02* (2013.01)

(58) Field of Classification Search
USPC ........................................................ 514/655
See application file for complete search history.

(56) References Cited

U.S. PATENT DOCUMENTS

| | | | |
|---|---|---|---|
| 4,831,057 A | 5/1989 | Reichert | 514/647 |
| 4,876,283 A | 10/1989 | Reichert | 514/562 |
| 5,458,879 A | 10/1995 | Singh et al. | 424/400 |
| 5,827,852 A | 10/1998 | Russell et al. | 514/255 |
| 6,663,889 B1 | 12/2003 | Maerz et al. | 424/464 |
| 7,179,849 B2 | 2/2007 | Terry | 523/122 |
| 7,223,418 B2 | 5/2007 | Hidaka et al. | 424/445 |
| 9,000,004 B2 | 4/2015 | Wang et al. | |
| 9,006,223 B2 | 4/2015 | Mahuran et al. | A61K 31/136 |
| 9,011,923 B2 | 4/2015 | Lewis et al. | A61K 9/50 |
| 9,016,221 B2 | 4/2015 | Brennan et al. | B08B 17/06 |
| 9,381,189 B2 | 7/2016 | Green et al. | A61K 31/4045 |
| 9,427,472 B2 | 8/2016 | Lichter et al. | A61K 47/34 |
| 9,447,108 B2 | 9/2016 | Fülöp et al. | C07D 489/02 |
| 2002/0064524 A1 | 5/2002 | Cevc | 424/94.63 |
| 2003/0166732 A1 | 9/2003 | Esperester et al. | 514/649 |
| 2003/0171391 A1 | 9/2003 | Gaida et al. | 514/282 |
| 2003/0216423 A1 | 11/2003 | Ulloa et al. | 514/290 |
| 2004/0132744 A1 | 7/2004 | Soldato | 514/255.04 |
| 2004/0248847 A1* | 12/2004 | Boldrini | A61K 9/0048 514/59 |
| 2005/0014844 A1 | 1/2005 | Gaida et al. | 514/650 |
| 2005/0014845 A1 | 1/2005 | Gaida et al. | 514/650 |
| 2005/0014847 A1 | 1/2005 | Gaida et al. | 514/640 |
| 2005/0266058 A1 | 12/2005 | Esperester et al. | 424/448 |
| 2007/0014833 A1* | 1/2007 | Milburn | A61K 31/05 424/427 |
| 2007/0184114 A1 | 8/2007 | Cevc | 424/484 |
| 2014/0206710 A1 | 7/2014 | Wang et al. | 514/291 |
| 2015/0044270 A1 | 2/2015 | McDonnell et al. | 424/428 |
| 2015/0056305 A1 | 2/2015 | Johnson et al. | 424/680 |
| 2015/0258081 A1 | 9/2015 | Lukas et al. | A61K 31/45 |
| 2016/0052931 A1 | 2/2016 | Fülöp et al. | C07D 489/02 |

FOREIGN PATENT DOCUMENTS

| | | | |
|---|---|---|---|
| DE | 10140320 | 3/2003 | A61K 35/78 |
| EP | 0240907 | 3/1987 | A61K 31/135 |
| EP | 1352646 | 10/2003 | A61K 9/20 |
| WO | WO9523591 | 9/1995 | A61K 9/10 |
| WO | WO03061642 | 7/2003 | A61K 31/136 |
| WO | WO03072094 | 9/2003 | A61K 31/136 |

OTHER PUBLICATIONS

International Search Report and Written Opinion issued in application No. PCT/US17/61108, dated Jan. 26, 2018 (6 pgs).
Beeh et al., "Antiflammatory Properties of Ambroxol," European Journal of Medical Research, Dec. 2008, vol. 13 (6 pgs).
Ben et al., "Upregulation of AQP3 and AQP5 induced by dexamethasone and ambroxol in A549 cells," Respiratory Physiology & Neurobiology, 2008 (8 pgs).
Bhattacharya et al., "Tear Production After Bilateral Main Lacrimal Gland Resection in Rabbits," The Association for Research in Vision and Ophthalmology, Inc., 2015 (10 pgs).
Floyd et al., "Mucin Deficiency Causes Functional and Structural Changes of the Ocular Surface," PLOS ONE, Dec. 2012, vol. 7, No. 12 (8 pgs).
Gibbs et al., "Ambroxol inhibits IgE-dependent mediator secretion from human skin mast cells," Inflamm Res., Apr. 2000, transcript only (3 pgs).
Gibbs et al., "Free radical scavengers differentially modulate anti-IgE-induced histamine release from human skin mast cells," Journal of Dermatological Science, Mar. 1998, vol. 16, No. 1, abstract only (3 pgs).
Gupta, P.R., "Ambroxol—Resurgence of an old molecule as an anti-inflammatory agent in chronic obstructive airway diseases," Lung India, 2010, vol. 27, No. 2 (4 pgs).
Ning et al., "Evaluating the Functionality of Conjunctiva Using a Rabbit Dry Eye Model," Journal of Ophthalmology, 2016 (10 pgs).
Office Action issued in U.S. Appl. No. 11/120,450, dated Apr. 9, 2010 (15 pgs).
Office Action issued in U.S. Appl. No. 11/120,450, dated Aug. 24, 2009 (19 pgs).
Office Action issued in U.S. Appl. No. 11/419,211, dated Aug. 6, 2009 (14 pgs).
Office Action issued in U.S. Appl. No. 11/751,245, dated Jun. 12, 2009 (11 pgs).
Preliminary Amendment Submitted Under 35 U.S.C. 371 for U.S. Appl. No. 12/063,874, dated Feb. 15, 2008 (3 pgs).

(Continued)

*Primary Examiner* — Marcos L Sznaidman
(74) *Attorney, Agent, or Firm* — Gavin J. Milczarek-Desai; Quarles & Brady LLP

(57) ABSTRACT

Formulations for treating ocular surface diseases, such as dry eye disease, and related methods are disclosed. The formulations include ambroxol or a chemical derivative thereof (for example, ambroxol hydrochloride) dispersed in a carrier and may optionally include a biocompatible polymer to provide extended release properties.

10 Claims, No Drawings

(56) References Cited

OTHER PUBLICATIONS

Response to Election/Restriction Requirement, U.S. Appl. No. 11/120,450, dated Apr. 2, 2009 (3 pgs).
Response to Office Action issued in U.S. Appl. No. 11/419,211, dated Oct. 30, 2009 (8 pgs).
Response to Office Action issued in U.S. Appl. No. 11/751,245, dated Oct. 27, 2009 (12 pgs).
Seagrave et al., "Effects of guaifenesin, N-acetylcysteine, and ambroxol on MUC5AC and mucociliary transport in primary differentiated human tracheal-bronchial cells," Respiratory Research, 2012, vol. 13, No. 98 (10 pgs).
Stevenson et al., "Is the main lacrimal gland indispensable? Contributions of the corneal and conjunctival epithelia," Survey of Ophthalmology, 2016, abstract only (1 pg).
Takeda et al., "Immunomodulatory Effects of Ambroxol on Airway Hyperresponsiveness and Inflammation," Immune Network, Jun. 2016, vol. 16, No. 3 (11 pgs).
Wang et al., "ENaC in the rabbit lacrimal gland and its changes during Sjögren's syndrome and pregnancy," Eye Contact Lens, Sep. 2015, vol. 41, No. 5 (16 pgs).
Wang et al., "MUC5AC Acts in Synchrony with Aquaporin 5 in Rabbit Conjunctiva in Acute Dry Eye Condition," Investigative Ophthalmology & Visual Science, Dec. 21, 2016, abstract only (1 pg).

\* cited by examiner

FORMULATIONS FOR THE TREATMENT OF OCULAR SURFACE DISEASES AND RELATED METHODS

CROSS REFERENCE TO RELATED APPLICATIONS

This application claims priority from U.S. Provisional Application Ser. Nos. 62/421,822, filed Nov. 14, 2016, and 62/463,717, filed Feb. 26, 2017, the contents of which are incorporated by reference herein.

BACKGROUND OF THE INVENTION

The ocular surface of the eye is a complex biological region that maintains corneal clarity, regulates tear film, and protects the eye from intrusions. Ocular surface diseases and disorders negatively affect the surface of the eye, including the cornea and the tear film. Ocular surface diseases include Dry Eye Disease (DED), chronic DED, otherwise known as "chronic dry eye syndrome," "dry eye syndrome," or "keratoconjunctivitis sicca." Symptoms of DED include unclear vision, irritation, itching, dryness, burning, light sensitivity, and possible loss of vision due to ocular surface damage. An estimated 3.2 million women and 1.68 million men aged 50 and over in the United States are affected by DED. The overall annual burden on the U.S. healthcare system from DED is estimated to be approximately $3.84 billion and the total estimated cost of DED on the population of the U.S. is estimated to be approximately $55.4 billion. The prevalence of DED increases linearly with age and appears to be higher in Asian populations.

SUMMARY OF THE INVENTION

Currently, dry eye is considered a multifactorial disease of the ocular surface characterized by a loss of homeostasis of the tear film, and accompanied by ocular symptoms, in which tear film instability and hyperosmolarity, ocular surface inflammation and damage, and neurosensory abnormalities play etiological roles. Formulations and methods of use are disclosed herein to treat ocular surface diseases, such as DED, and related conditions. The disclosed formulations include Ambroxol and/or one or more derivatives thereof, dispersed in a carrier. The carrier may be water-based (for example, a sterile saline solution) and may include various additives, such as lubricants, preservatives, ionic species, pH-adjusting agents, or other desired additives. In some embodiments, the disclosed formulations include at least one biocompatible polymer dissolved in the carrier to provide extended release of the ambroxol or chemical derivative. Or, biocompatible polymer(s) impregnated with the ambroxol or its chemical derivatives as a vehicle provides extended release of the drug. The disclosed formulations are designed for topical application to the eye and may take the form of a solution, gel, drop, ointment, suspension, microemulsion, nanoparticulate dispersion, liposome, lotion, and/or paste, etc. The formulations described herein can be applied to the eye in any suitable manner, such as manually (for example, with eye drops) or with a device that controllably releases the formulation over a predetermined period of time.

DETAILED DESCRIPTION

The current clinical approach to treating DED includes topical application of lubricants for mucosa protection, procedures to slow tear drainage (for example, punctal occlusion, whereby punctal plugs are inserted into the tear drainage canal of the eye to prolong tear residence time), therapies to improve meibomian gland function in the lid to retard the evaporation of tears, eye shields (such as in the form of moisture chamber for the eyes), and administering anti-inflammatory agents. Outside the United States, treatment for DED also can include stimulating water secretion and/or mucus secretion in the eye.

However, a large portion of DED patients remains in whom current clinical approaches generally do not provide sufficient symptom relief. Additionally, ongoing treatment efforts (for example, frequent and regular use of eye drops) can be tedious, demanding (relative to routine busy daily schedules) and expensive.

Various formulations for topical application to the eye for the treatment of DED and related symptoms are described herein. The disclosed formulations and related methods differ from previous treatment approaches. Specifically, the formulations disclosed herein include compounds capable of stimulating the conjunctiva (the mucosal membrane covering the eyeball and the eyelid surface), which studies indicate can contribute to the maintenance of tear film homeostasis on the ocular surface such as in regulating the quantity and quality of tear film.

The disclosed formulations may improve and, in some cases, cure ocular surface diseases, such as DED. The disclosed formulations can be produced in any suitable form, including but not limited to solutions, gels, drops, creams, ointments, suspensions, dispersions, nanoparticulate dispersions, emulsions, microemulsions, liposomes, pastes, or other desired forms. The disclosed formulations comprise ambroxol and/or a derivative thereof. Ambroxol, as referenced herein, has the following chemical formula:

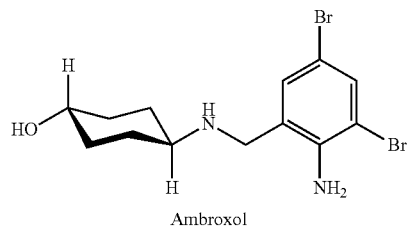

Ambroxol

Ambroxol is a commercially available synthetic mucolytic drug that is sometimes used to stimulate surfactant synthesis in the lung to treat respiratory diseases associated with viscid or excessive mucus. Ambroxol is an active ingredient in cough syrup and is also available as a tablet, pastille, dry powder sachet, inhalation solution, drop, ampule, and effervescent tablet. Prior to the filing of the subject application and its priority documents, there had not been any indication that ambroxol or any of its chemical derivatives would be useful for treating eye conditions, such as ocular surface disease or DED.

As used herein, the terms "ambroxol derivatives" and "chemical derivatives of ambroxol" refer to compounds derived from ambroxol, precursor compounds for ambroxol, and salt forms of ambroxol, for example, the acid addition salt ambroxol hydrochloride [trans-4-(2-amino-3,5-dibromobenzyl amino)cyclohexanol hydrochloride]. In some embodiments, more than one form of ambroxol may be included in a single formulation. For example, in some embodiments, a formulation may include at least a first ambroxol derivative and at least a second ambroxol derivative. In these and other embodiments, the formulation may also comprise ambroxol.

In some embodiments, the total concentration of ambroxol and chemical derivatives thereof (if present) may be between 0.01% and 20% by weight based on the total weight of the formulation (w/w). In these and other embodiments, the total concentration of ambroxol and chemical derivatives thereof (if present) may be between 0.01% and 20% by weight based on the total volume of the formulation (w/v), preferably between 0.02 and 10% (w/v). In preferred embodiments, the total concentration of ambroxol and chemical derivatives thereof in the formulation is between 0.5 and 5% (w/v). The disclosed formulations also include a carrier in which the ambroxol and/or ambroxol derivative(s) are dispersed. In some embodiments, the carrier may be a buffered saline solution, but also may be an ointment, gel or paste.

The disclosed formulations may also, in some embodiments, include an extended-release vehicle, such as a biocompatible polymer, dissolved in the carrier or by itself impregnated with ambroxol to hold the ambroxol and slowly release it into the tear film or onto the ocular surface, preferably for an extended release period of up to six months. The biocompatible polymer may be biodegradable or non-biodegradable, depending on desired use and application schedule. Example biocompatible polymers that may be used in the disclosed formulations as an extended-release vehicle include but are not limited to poly-2-hydroxyethyl-methacrylate (p-HEMA hydrogels), poly(lactic-co-glycolic) acid (PLGA), polycaprolactone (PCL), hydroxypropyl cellulose, Anecortave acetate (AnA), gelatin, and/or collagen. The inclusion of an extended-release vehicle may, in some cases, allow for less frequent application while still providing relief from DED symptoms.

In some embodiments, the disclosed formulations may also include one or more additives. Additives that may be included in the disclosed formulations include but are not limited to demulcents, preservatives, emollients, ionic species, pH-adjusting agents, and other possible additives. Example demulcents that may be used in the disclosed formulations include glycerin, carboxymethylcellulose, hydroxyethyl cellulose, hydroxypropyl methylcellulose, methylcellulose, dextran 70, gelatin, polyethylene glycol 300, polyethylene glycol 400, polysorbate 80, polyvinyl alcohol, povidone, etc. Examples of preservatives that may be used in the disclosed formulations include benzalkonium chloride and other known preservatives, such as chlorobutanol. Emollients may include lanolin preparations, various mineral oils, Omega 3, paraffin, petroleum and waxes. Zinc and or sodium ions may be included in the disclosed formulation as an ionic species, in some embodiments. Possible pH-adjusting agents that may be used include citrate buffers (e.g., sodium citrate), borate buffers (e.g., sodium borate), and other acidic or basic compounds. Numerous configurations and variations of additives may be used in the disclosed formulations.

Some research studies indicate that osmotically-driven water transport across conjunctival cell membranes is primarily mediated by water channels called aquaporins (AQPs), which maintain tear volume and regulate osmolarity at the ocular surface. In particular, elevation of AQP5 expression in the conjunctiva has been shown to lead to increased production of Mucin 5AC (MUC5AC), a major gel-forming mucin in tear film. Accordingly, agents that stimulate AQPs in the conjunctiva may also stimulate mucin secretion. Prior to the filing of the subject application, some research indicated that ambroxol can stimulate the expression of AQP5 in human airway epithelial cells. See *Upregulation of AQP3 and AQP5 Induced by Dexamethasone and Ambroxol in A459 Cells* by Ben et al, Respiratory Physiology & Neurobiology 161 (2008) 111-118. The disclosed formulations may, in some circumstances, stimulate AQPs and MUC5AC in the conjunctiva, thereby improving or relieving symptoms of DED. Additionally, Ambroxol and chemical derivatives thereof have analgesic as well as anti-inflammatory properties, which may further help relieve eye discomfort, improve tear film homeostasis and/or restore ocular surface health. In some cases, treatment with the disclosed formulations may alleviate DED symptoms, such as unclear vision, irritation, itching, dryness, burning, and/or light sensitivity.

Frequency of topical application to a subject (for example, a human or animal) may vary between patients. For example, in some circumstances, the disclosed formulations may be applied as frequently as once every ten minutes or as infrequently as once every day. The formulation may be applied once, twice, three times or more over a period of one day, two days, three days, four days, five days, or more than five days. In some embodiments where an extended-release vehicle is included in the formulation, the formulation may be topically applied with a frequency of at least one time a day to one time a week, or one time a month to one time every six months. Frequency of topical application can be determined by numerous considerations, including level of symptom relief provided, pain relief experienced, as well as other pertinent health considerations, such as possible drug interactions.

The disclosed formulations may be administered using any desired technique. For example, in some cases, the formulations may be eye drops that are administered manually by a user. In other cases, the formulations may be topically applied as a gel or ointment directly to a desired region of the eye using a swab or other type of applicator. In some embodiments, the disclosed formulations may be delivered using a device designed for immediate formulation release or extended formulation release. For example, in some embodiments, the formulation may be delivered using one or more of the following devices: external pumps, contact lenses, punctal plugs, muco-adhesive tablets, pills, capsules, pellets, particles, plasters, an ocular insert device, strips placed onto the conjunctiva or cornea, conjunctival inserts or depots, subconjunctival, subtenon, and intravitreal injections, or another suitable types of device.

Efficacy of the formulation in a subject can be assessed by numerous techniques. For example, a patient may self-report symptom relief experienced. In other cases, the eye may be visually assessed or clinical tests, such as the Schirmer's Test, wherein paper strips are inserted into the eye for several minutes to measure tear production, may be used to assess formulation efficacy.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes, and not to limit the scope of the inventive subject matter described herein. The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

We claim:

1. A method of treating dry eye disease, the method comprising topically administering to an ocular surface a formulation comprising ambroxol and/or a salt form of ambroxol in a weight percent of between 0.01% and 20%, based on total weight or total volume of the formulation, and a carrier comprising a buffered saline solution to a subject suffering from dry eye disease.

2. The method of claim 1, wherein the formulation is administered to the subject at least once a day for a period of at least five days.

3. The method of claim 1, wherein the formulation is administered to the subject using a device that provides continuous application of the formulation.

4. The method of claim 1, wherein after administration, the subject experiences relief from some or all dry eye disease symptoms.

5. The method of claim 1, wherein the ambroxol and/or a salt form of ambroxol is present in the formulation in a weight percent of between 0.02% and 10% based on total weight or total volume of the formulation.

6. The method of claim 1, wherein the ambroxol and/or a salt form of ambroxol is present in the formulation in a weight percent of between 0.5 and 5% based on total weight or total volume of the formulation.

7. The method of claim 1, wherein the formulation further comprises a biocompatible polymer dissolved in the carrier or ambroxol impregnated within a biocompatible polymer.

8. The method of claim 7, wherein the biocompatible polymer is poly-2-hydroxyethylmethacrylate (p-HEMA hydrogels), poly(lactic-co-glycolic) acid (PLGA), poly-caprolactone (PCL), hydroxypropyl cellulose, Anecortave acetate (AnA), gelatin, and/or collagen.

9. The method of claim 1, wherein the salt form of ambroxol is trans-4-(2-amino-3,5-dibromobenylamino) cyclohexanol hydrochloride.

10. The method of claim 1, wherein the ambroxol and/or a salt form of ambroxol is present in a weight percent of between 0.01 and 2% based on total weight or total volume of the formulation.

* * * * *